US00PP36349P2

(12) United States Plant Patent
Vandenberg

(10) Patent No.: US PP36,349 P2
(45) Date of Patent: Dec. 31, 2024

(54) ***HIBISCUS* PLANT NAMED 'Peach Ripple Wind'**

(50) Latin Name: *Hibiscus rosa-sinensis*
Varietal Denomination: Peach Ripple Wind

(71) Applicant: Cornelis P. Vandenberg, Fort Myers, FL (US)

(72) Inventor: Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 0 days.

(21) Appl. No.: 18/395,597

(22) Filed: Dec. 24, 2023

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Hibiscus* plant named 'Peach Ripple Wind', characterized by its upright to somewhat outwardly spreading and uniformly mounded plant habit appropriate for container production; freely branching habit, dense and bushy appearance; glossy dark green-colored leaves; uniform, freely and early flowering habit; orange-colored flowers with dark red-colored throats; and good postproduction and garden performance.

1 Drawing Sheet

Botanical designation: *Hibiscus rosa-sinensis.*
Cultivar denomination: 'PEACH RIPPLE WIND'.

BACKGROUND OF THE INVENTION

The present invention relates to a new and distinct *Hibiscus* plant, botanically known as *Hibiscus rosa-sinensis* and hereinafter referred to by the name 'Peach Ripple Wind'.

The new *Hibiscus* plant is a product of a planned breeding program conducted by the Inventor in Alva, Florida. The objective of the breeding program is to create new freely-branching *Hibiscus* plants with uniform plant habit appropriate for container production, early and freely flowering habit, desirable flower color, good garden performance and resistance to Bacterial Leaf Spot.

The new *Hibiscus* plant originated from a cross-pollination made by the Inventor in Alva, Florida in 2017 of *Hibiscus rosa-sinensis* 'Cayman Wind', disclosed in U.S. Plant Pat. No. 23,760, as the female, or seed, parent with a proprietary breeding selection of *Hibiscus rosa-sinensis* identified as code number 4010, not patented, as the male, or pollen, parent. The new *Hibiscus* plant was discovered and selected by the Inventor as a single flowering plant within the progeny of the stated cross-pollination in a controlled greenhouse environment in Alva, Florida on Jan. 11, 2020.

Asexual reproduction of the new *Hibiscus* plant by vegetative terminal cuttings in a controlled greenhouse environment in Alva, Florida since March 2020 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Peach Ripple Wind'. These characteristics in combination distinguish 'Peach Ripple Wind' as a new and distinct *Hibiscus* plant:

1. Upright to somewhat outwardly spreading and uniformly mounded plant habit appropriate for container production.
2. Freely branching habit, dense and bushy appearance.
3. Glossy dark green-colored leaves.
4. Uniform, freely and early flowering habit.
5. Orange-colored flowers with dark red-colored throats.
6. Good postproduction and garden performance.

Plants of the new *Hibiscus* can be compared to plants of the female parent, 'Cayman Wind'. Plants of the new *Hibiscus* differ primarily from plants of 'Cayman Wind' in the following characteristics:

1. Flowers of plants of the new *Hibiscus* are flatter than and not as reflexing as plants of 'Cayman Wind'.
2. Flowers of plants of the new *Hibiscus* are orange in color with dark red-colored throats whereas flowers of plants of 'Cayman Wind' are pink in color with dark red-colored throats.

Plants of the new *Hibiscus* can be compared to plants of the male parent selection. Plants of the new *Hibiscus* differ primarily from plants of the male parent selection in the following characteristics:

1. Plants of the new *Hibiscus* are more freely branching than plants of the male parent selection.
2. Flowers of plants of the new *Hibiscus* are orange in color with dark red-colored throats whereas flowers of plants of the male parent selection are yellow in color with dark red-colored throats.

Plants of the new *Hibiscus* can be compared to plants of the *Hibiscus rosa-sinensis* 'Orange Lava Wind', disclosed in U.S. Plant Pat. No. 35,219. In side-by-side comparisons plants of the new *Hibiscus* differ from plants of 'Orange Lava Wind' in the following characteristics:

1. Flowers of plants of the new *Hibiscus* are slightly smaller than flowers of plants of 'Orange Lava Wind'.
2. Flowers of plants of the new *Hibiscus* are orange in color with dark red-colored throats whereas flowers of plants of 'Orange Lava Wind' are bright orange in color with dark red-colored centers.

BRIEF DESCRIPTION OF THE PHOTOGRAPH

The accompanying colored photograph illustrates the overall appearance of the new *Hibiscus* plant showing the colors as true as it is reasonably possible to obtain in colored reproductions of this type. Colors in the photograph may differ slightly from the color values cited in the detailed botanical description which accurately describe the colors of the new *Hibiscus* plant. The photograph is a side perspective view of a typical flowering plant of 'Peach Ripple Wind' grown in a container.

DETAILED BOTANICAL DESCRIPTION

The aforementioned photograph and following observations, measurements and values describe plants grown during the summer and early autumn in 15-cm containers in a polyethylene-covered greenhouse in Alva, Florida under cultural practices which closely approximate commercial *Hibiscus* production. During the production of the plants, day temperatures averaged 28° C., night temperatures averaged 18° C. and light levels averaged 4,500 foot-candles. Plants were pinched two times and were seven months old when the photograph and the description were taken. In the description, color references are made to The Royal Horticultural Society Colour Chart, 2015 Edition, except where general terms of ordinary dictionary significance are used.

Botanical classification: *Hibiscus rosa-sinensis* 'Peach Ripple Wind'.

Parentage:

*Female, or seed, parent.*—*Hibiscus rosa-sinensis* 'Cayman Wind', disclosed in U.S. Plant Pat. No. 23,760.

*Male or pollen parent.*—Proprietary breeding selection of *Hibiscus rosa-sinensis* identified as code number 4010, not patented.

Propagation:

*Type.*—By vegetative terminal cuttings.

*Time to initiate roots, summer and winter.*—About four to five weeks.

*Time to produce a rooted young plant, summer and winter.*—About five to six weeks.

*Root description.*—Thick, fibrous; typically white to light brown in color, actual color of the roots is dependent on substrate composition, water quality, fertilizer, substrate temperature and physiological age of roots.

*Rooting habit.*—Moderate branching; moderately dense.

Plant description:

*Plant form and growth habit.*—Perennial, evergreen, upright to somewhat outwardly spreading and uniformly mounded plant habit; moderately vigorous to vigorous growth habit.

*Branching habit.*—Freely branching habit with lateral branches potentially develop at every node; pinching enhances lateral branch development; dense and bushy appearance.

*Plant height.*—About 29 cm to 30 cm.

*Plant diameter* (*area of spread*).—About 34 cm to 35 cm.

Lateral branch description:

*Length.*—About 20.5 cm.

*Diameter.*—About 8 cm to 9 cm.

*Internode length.*—About 2.2 cm to 2.6 cm.

*Aspect.*—Upright to somewhat outwardly spreading.

*Texture and luster, immature.*—Smooth; glossy.

*Texture and luster, mature.*—Woody and rough; matte.

*Color, immature.*—Close to 144A.

*Color, mature.*—Close to between 197B and 199B.

Leaf description:

*Arrangement.*—Alternate, single; numerous; symmetrical.

*Length.*—About 8 cm.

*Width.*—About 7 cm.

*Shape.*—Broadly ovate.

*Apex.*—Rounded acute.

*Base.*—Truncate with obtuse tendencies.

*Margin.*—Crenate.

*Texture and luster, upper and lower surfaces.*—Smooth, glabrous; glossy.

*Venation pattern.*—Pinnate; arcuate.

*Color.*—Developing leaves, upper and lower surfaces: Close to 146A. Fully expanded leaves, upper surface: Close to 147A; venation, close to 146A Fully expanded leaves, lower surface: Close to 147B; venation, close to 144A.

*Petioles.*—Length: About 2.2 cm to 2.4 cm. Diameter: About 3 mm. Texture and luster, upper and lower surfaces: Smooth, glabrous; moderately glossy. Color, upper and lower surfaces: Close to 144A.

Flower description:

*Flower arrangement and flowering habit.*—Rounded single flowers arranged at terminal leaf axils; uniform and freely flowering habit with about two to three flowers per terminal; flowers face mostly upright to outwardly.

*Natural flowering season.*—Plants of the new *Hibiscus* flower naturally during the spring and summer or during periods of warm weather; plants flower year-round in the greenhouse.

*Flower longevity.*—Depending on temperature and water status, flowers typically last about two to three days on the plant; flowers persistent.

*Flower diameter.*—About 13 cm to 14 cm.

*Flower length* (*height*).—About 7.5 cm to 7.75 cm.

*Flower buds.*—Resistance to abscission during shipping: Plants of the new *Hibiscus* have been observed to resist flower bud drop during shipping. Length: About 1.8 cm to 2 cm. Diameter: About 1.2 cm. Shape: Ovoid. Texture and luster: Smooth, glabrous; moderately glossy. Color: Close to 144A.

*Petals.*—Arrangement: Corolla consists of a single whorl of five petals that are fused at base; petals imbricate. Length: About 7 cm to 7.25 cm. Width: About 7 cm. Shape: Spatulate. Apex: Broadly obtuse. Base: Cuneate. Margin: Entire, ruffled. Texture and luster, upper and lower surfaces: Smooth, glabrous; matte except for upper surface's glossy center. Color: When opening and fully opened, upper surface: Close to 24A; towards the center, close to 53B to 53C; venation, close to N25A. When opening and fully opened, lower surface: Close to 24B to 24C; towards the base, close to 51A; venation, close to 20A.

*Sepals*.—Appearance: Five sepals in a single whorl fused into a tubular star-shaped calyx. Length: About 2.4 cm. Width: About 1.1 cm. Shape: Narrowly deltoid. Apex: Sharply acute. Margin: Entire. Texture and luster, upper surface: Smooth, glabrous; glossy. Texture and luster, lower surface: Smooth, glabrous; moderately glossy Color, upper and lower surfaces: Close to 144A.

*Epicalyx*.—Quantity and arrangement: About six to seven in a single whorl fused at base. Length: About 1.1 cm to 1.3 cm. Width: About 3.5 mm to 4 mm. Shape: Acicular. Apex: Sharply acute. Margin: Entire; not undulate. Texture and luster, upper surface: Smooth, glabrous; moderately glossy. Texture and luster, lower surface: Smooth, glabrous; matte. Color, upper surface: Close to 146A. Color, lower surface: Close to 147A.

*Peduncles*.—Length: About 1.4 cm to 1.75 cm. Diameter: About 4 mm to 5 mm. Aspect: Upright. Strength: Strong, not flexible. Texture and luster: Smooth, glabrous; moderately glossy. Color: Close to 144A.

*Reproductive organs*.—Androecium: Stamen number: Numerous, about 50 to 56. Filament length: About 5 mm to 6 mm. Filament color: Close to 25C. Anther shape: Oblong. Anther length: About 1.5 mm. Anther color: Close to 12A. Amount of pollen: None observed. Gynoecium: Pistil number: One per flower. Pistil length: About 6.5 cm to 6.7 cm. Style length: About 5.5 cm to 5.8 cm. Style texture and luster: Smooth, glabrous; glossy. Style color: Close to N25A. Stigma appearance: Five-parted, rounded. Stigma color: Close to 46A. Ovary color: Close to 154D.

*Seeds and fruits*.—To date, seed and fruit production has not been observed on plants of the new *Hibiscus*.

Garden performance: Plants of the new *Hibiscus* have been observed to have good garden performance and to tolerate wind, rain and temperatures ranging from about 2° C. to about 40° C.

Pathogen & pest resistance: To date, plants of the new *Hibiscus* grown under Florida production conditions have not been shown to be resistant to pests and other pathogens common to *Hibiscus* plants.

It is claimed:

1. A new and distinct *Hibiscus* plant named 'Peach Ripple Wind' as herein illustrated and described.

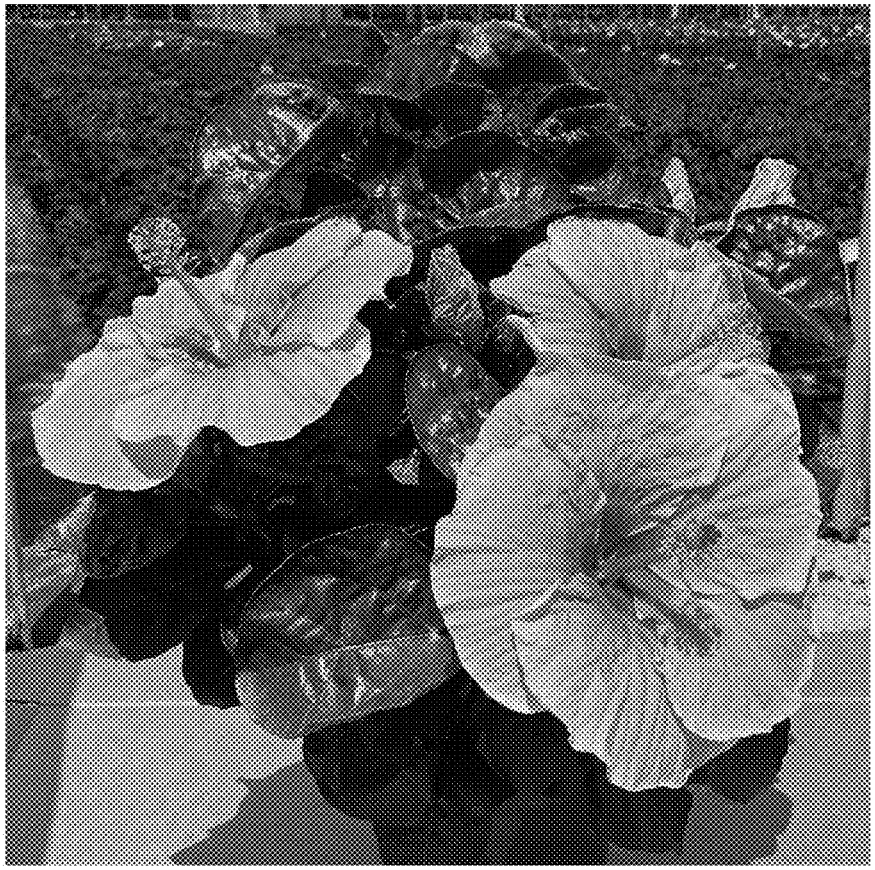

* * * * *